(12) United States Patent
Caretti et al.

(10) Patent No.: US 7,538,800 B1
(45) Date of Patent: May 26, 2009

(54) METHODS AND APPARATUS FOR ASSESSING VISIBILITY THROUGH AN OPTICAL MATERIAL

(75) Inventors: David M. Caretti, Bel Air, MD (US); Karen M. Coyne, Baltimore, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 788 days.

(21) Appl. No.: 11/240,781

(22) Filed: Sep. 27, 2005

(51) Int. Cl.
*H04N 9/73* (2006.01)
(52) U.S. Cl. ............... 348/227.1; 348/180; 348/234
(58) Field of Classification Search ............ 348/180, 348/207.99, 222.1, 234, 227.1; 356/239.1, 356/432
See application file for complete search history.

(56) References Cited

U.S. PATENT DOCUMENTS 5,987,152 A * 11/1999 Weisser .................... 382/104
6,128,088 A * 10/2000 Nishiwaki ................. 356/392
6,559,939 B1 * 5/2003 Saunders ................ 356/239.1
6,853,453 B2 * 2/2005 Kwon ....................... 356/437
7,011,411 B2 * 3/2006 Shibutani et al. ........... 351/211

* cited by examiner

*Primary Examiner*—Lin Ye
*Assistant Examiner*—Gevell Selby
(74) *Attorney, Agent, or Firm*—Ulysses John Biffoni

(57) ABSTRACT

Assessing visibility through an optical material by capturing a digital image of a target through the material, determining its intensity, and using such intensity to determine a visual acuity index for the material. An apparatus for performing the method can assess visibility through an optical material exposed to environmental conditions. The apparatus includes an imaging system with a camera for acquiring digital images of the target through the optical material, a system for exposing the material to environmental conditions, and a system for processing intensities of the target in the acquired digital images. The processing system includes programming for relating the intensity of the target to the visual acuity index, whereby visibility through the optical material is determined.

23 Claims, 4 Drawing Sheets

METHODS AND APPARATUS FOR ASSESSING VISIBILITY THROUGH AN OPTICAL MATERIAL

GOVERNMENTAL INTEREST

The invention described herein may be manufactured, used and licensed by or for the U.S. Government.

TECHNICAL FIELD

This document relates to methods and apparatus for assessing visibility through an optical material.

BACKGROUND

Goggles, respirators, masks, helmets, eyewear, protective devices, and the like generally include lenses, visors, windows or other transparent or translucent optical materials for the user to look through. It is important to be able to see through such optical materials, in whatever form or shape they may take. Unfortunately, the visibility through such optical materials is sometimes compromised by environmental conditions. For example, optical materials in goggles, masks, or other protective devices sometimes get fogged by the user's respiration, by differences in temperature or humidity, or by other environmental factors such as the adsorption or deposition of smoke or other airborne particles.

It is useful to assess the performance of the optical materials of a particular device or configuration by evaluating the reduction in visibility through the optical materials due to fogging or other environmental factors. Such assessments can be difficult, however, especially when performance is assessed under a variety of conditions, or by different investigators or parties within a commercial production chain. Although lens fogging tests have been performed in the past, the results have generally been expressed in terms that are divorced from a meaningful assessment of visibility. For example, prior art methods of measuring performance of optical materials have largely been subjective, and have often failed to provide meaningful results that are applicable to a wide range of optical materials or environmental conditions.

SUMMARY

According to one aspect of the invention, a method of assessing visibility through an optical material includes capturing a digital image of a target through the optical material and determining the intensity of the target. Once determined, the target intensity is used to determine a visual acuity index of the optical material. The visual acuity index is one objective measure corresponding to visibility through the optical material.

According to another aspect of the invention, the foregoing method of assessing visibility through an optical material is accomplished by an apparatus, and such apparatus can be used for assessing the visibility through an optical material that has been exposed to one or more environmental conditions that effect visibility. The one or more environmental conditions can include smoke or fogging. The apparatus includes an imaging system with a camera located and oriented to acquire digital images of the target through the optical material. The apparatus also includes a system for exposing the optical material to one or more environmental conditions, such as smoke or fogging, as well as a system for processing the digital images. The processing system includes suitable programming for determining the intensity of the target appearing in the digital image or images and for relating the intensity to a visual acuity index so that visibility through the optical material can be assessed.

According to still another aspect of the invention, the intensity of the target is related to the Snellen visual acuity index by using either a correlation file or a correlation equation. The correlation file or correlation equation, in turn, is determined by correlating or calibrating the target intensities when viewed through optical materials having known or pre-determined visual acuity indices associated therewith.

According to yet another aspect of the invention, the apparatus for assessing visibility through an optical material includes a headform operatively associated with the imaging system and the system for exposing the optical material to one or more environmental conditions.

The above-described apparatus and methods are not limited to assessing the visibility through an optical material exposed to one or more environmental conditions, but can likewise be used to determine visibility through optical materials divorced from the effects of environmental conditions.

DESCRIPTION OF DRAWINGS

Like reference symbols in the various drawings indicate like elements.

DETAILED DESCRIPTION

Figure 1:
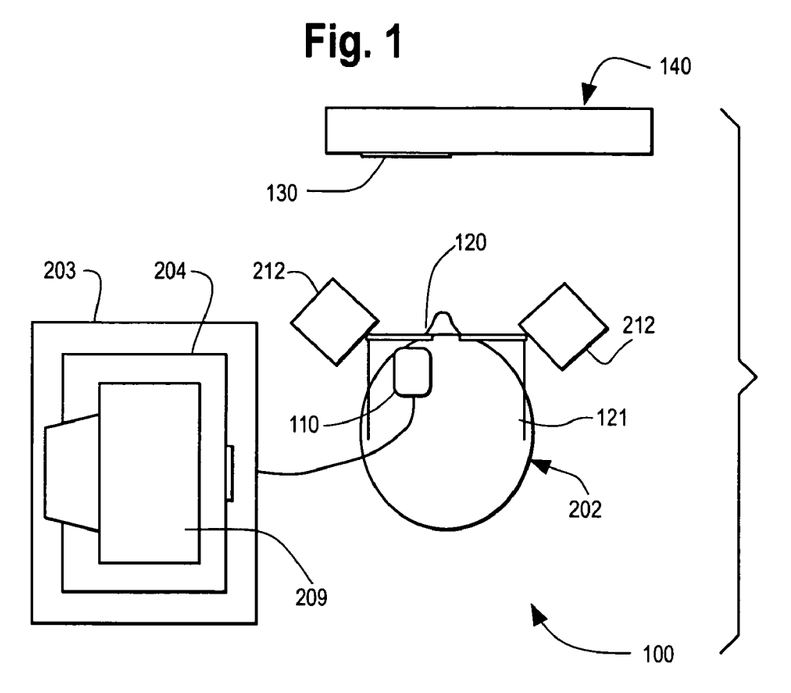
FIG. 1 is a top view, partly schematic, of an apparatus suitable for implementing principles of the present invention.

One suitable apparatus for assessing visibility through optical materials is shown generally and schematically in FIG. 1. An apparatus 100 has an imaging system 110. In this particular implementation, apparatus 100 is configured to assess the visibility through optical material 120 of a protective facemask 121. However, it is noted that any number of optical materials with or without associated masks, eyewear, etc., can likewise be evaluated by the apparatus 100 shown in FIG. 1. Protective facemask 121 is suitably associated with a mount in the form of headform 202. Imaging system 110 is operatively associated with headform 202 so that images can be captured at locations corresponding to one or both "eyes" of headform 202.

Visibility through optical material 120 is assessed by acquiring and processing images of a suitable target 130 as "seen" by imaging system 110 through optical material 120, as will be discussed in more detail subsequently. The images of target 130 that are captured by imaging system 110 are processed by any suitable computer system or other image processing system shown schematically at 203.

Apparatus 100 includes suitable software, instructions, or other processing steps to relate the intensity of the target seen through optical material 120 to a relatively objective visual acuity index, such as the Snellen index (20/20, 20/40, 20/100, 20/200, etc). In this way, apparatus 100 may be used to determine visibility through certain types of optical materials in certain types of eyewear, protective masks, goggles, and the like, under any number of environmental conditions, including so-called "fogging" conditions due to respiration, at any given point in time, or after lapse of any given amount of time.

Tests using apparatus 100 can hold any number of variables constant, while changing optical materials, environmental conditions, and any other variables. Since the results of such tests relate to a relatively objective standard of visual acuity, such as the Snellen index, the results permit comparison of visibility through different optical materials mounted in different configurations in protective masks and the like, and subject to different breathing patterns, temperatures, and other environmental conditions. The availability of objective results pertaining to visibility permits an overall evaluation of performance of optical materials by apparatus 100.

Figure 2:
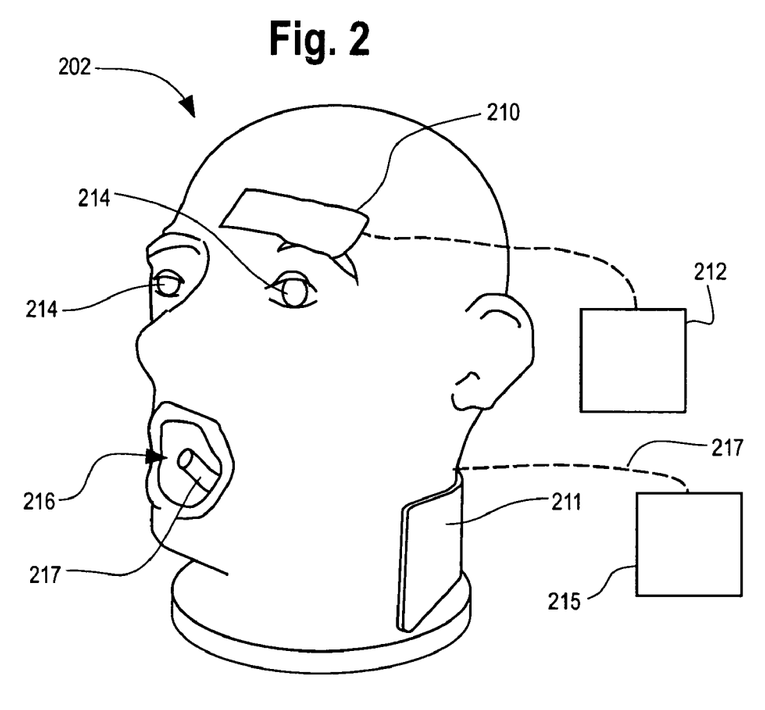
FIG. 2 is a perspective view of a headform suitable for use in evaluating optical materials worn over a user's eyes, in connection with an embodiment such as that shown in FIG. 1.

Having discussed apparatus 100 generally with reference to FIG. 1, headform 202 is shown in more detail in FIG. 2. Headform 202 is configured to hold imaging system 110 and optical material 120 relative to each other so that imaging system 110 "looks through" optical material 120. Although it will be recognized that any number of mounting structures could secure these components relative to each other in this manner, headform 202, which simulates a human head, has been found suitable. Acquiring lens 111 (FIG. 3) of imaging system 110 is suitably positioned to look through eye hole 214 or, of course, can simply be mounted at a location approximating the location of human eyes. Optical material 120, as shown in FIG. 1, is suitably mounted to headform 202 to cover eye holes 214 so that acquiring lens 111 of imaging system 110 must capture image 130 (FIG. 1) through optical material 120. An acquiring lens of imaging system 110 may be located in either or both eyeholes 214, or multiple imaging systems 110 may be used in any desired configuration to assess visibility through optical material 120.

Apparatus 100 may be optionally equipped with mechanisms or means to expose optical material 120 to one or more environmental conditions. In this way, visibility through optical material 120 can be tested under different environmental conditions. In one implementation, apparatus 100 includes a system adapted to test whether, and by how much, visibility through optical material 120 is reduced by the "fogging" of optical material 120 from exposure to differences in temperature, humidity, or respiration that are associated with the wearing of the associated protective mask. In another implementation, apparatus 100 includes a system adapted to test whether, and by how much, visibility through optical material 120 is reduced by exposing the optical material to smoke or other particulates that may be adsorbed by or deposited onto the optical material 120.

In the fogging implementation, the system for fogging optical material 120 includes certain components to be described, however, fogging can be achieved in a variety of ways. One way to fog optical material 120, which simulates the humidity associated with the evaporation of perspiration from human skin, involves supplying moisture to an absorbent material such as cotton that is secured to headform 202 so that evaporation from the material contacts and condenses upon the surface of optical material 120. As shown in FIG. 2, absorbent material 210 is secured to headform 202 at a location enclosed by mask 121, such as on the "forehead" of headform 202. Moisture is supplied to absorbent material 210 by any suitable means, such as a dual-channel peristaltic pump 212 operatively connected to headform 202 and absorbent material 210.

To simulate body temperature, apparatus 100 includes a heater 211 connected to headform 202 in a manner suitable to warm the exterior surface of headform 202 to 34° C., the surface temperature of human skin on the head. One suitable heater 211 is a KAPTON band heater, which is shown affixed to the base of the "neck" of headform 202. Any suitable means for regulating and monitoring the temperature of headform 202 is likewise included in apparatus 100. For example, a proportional, integrative, derivative temperature controller and a thermistor, such as a YSI 400 Series thermistor available from Yellow Springs, International (not shown), located within headform 202 proximate to the forehead, have been found suitable. Any other locations in thermal communication with headform 202 are also suitable, as are other mechanisms for monitoring and regulating the temperature of headform 202.

Apparatus 100 optionally permits simulation of the effect of breathing on visibility through optical material 120. In particular, headform 202 has a "mouth" 216 configured to operatively connect to a breathing mechanism 215 to simulate the effects of breathing. For example, in the case where protective mask 121 constitutes a full-face respirator, a portion of mask 121 encloses mouth 216, and breathing mechanism 215 is in the form of a breathing pump, which inhales and exhales by pushing air out or pulling air through mouth tube 217. Mouth tube 217 has an end located proximate to or within mouth 216 as shown, and has an opposite end in pneumatic communication with breathing pump 215. Use of breathing pump 215 allows air to be drawn across the inside surface of optical material 120 when such optical material 120 is in the form of the lens or visor of protective mask 121.

Figure 3:
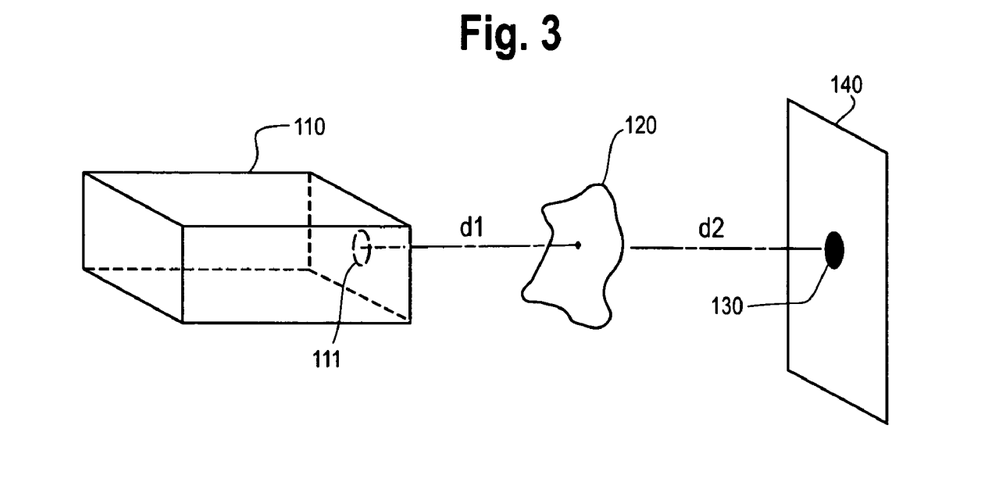
FIG. 3 is a schematic representation of one suitable imaging system useful in connection with the apparatus and headform of FIGS. 1 and 2.

Referring now more particularly to FIG. 3, the imaging system 110 is a charge coupled device (CCD) camera, and is operable to obtain a digital image of target 130. One suitable CCD camera is a 30 mm (W)×30 mm (H)×26 mm (D) black and white CCD camera with a 920 field of view. Imaging lens 111 is oriented to capture an image of target 130 through optical material 120 and is separated from the optical material 120 by a first distance $d_1$. While distance $d_1$ may be any distance suitable for the particular device being tested, in this implementation, $d_1$ is the distance between the lens 120 of mask 121 and the imaging lens 111 of imaging system 110.

The target 130 may be any two-dimensional shape or three-dimensional object. In this embodiment, the target 130 is one or more dark or gray-scale circles having a diameter of one inch. The target is mounted or affixed to a contrasting backing 140, and is separated from the optical material by a distance $d_2$ (which may be any suitable distance). In this implementation, $d_2$ is approximately one foot.

Imaging system 110 is operable to record or otherwise acquire or capture a digital image of target 130 through optical material 120. Depending on the testing, either a single digital image of the target 130 may be acquired, or a series of digital images of the target may be taken.

Figure 4A:
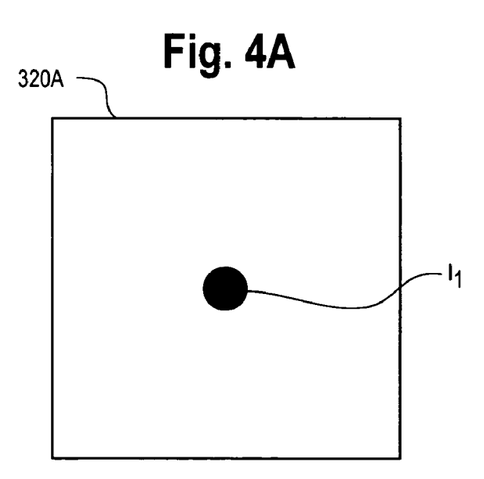
FIGS. 4A and 4B illustrate two images of a target as acquired by the imaging system of FIG. 3.
Figure 4B:
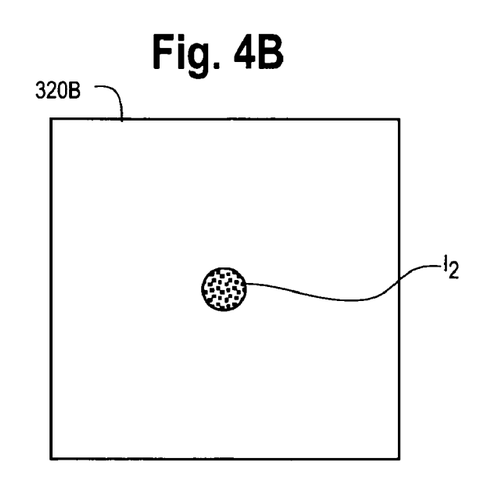

Two exemplary digital images captured by imaging system 110 of apparatus 100 are shown in schematic form in FIGS. 4A and 4B. Image 320A was captured under a first set of variables, including a particular optical material, as well as associated environmental conditions; whereas image 320B was captured under a second set of variables, including potentially a second optical material and/or a second set of environmental conditions. Whatever the optical material or environmental conditions, images 320A and 320B as captured by imaging system 110 are analyzed or otherwise processed through a suitable processing system 203, as discussed subsequently. Digital images, such as those of 320A and 320B, are saved in a suitable format for processing system 203, such as a JPEG file, GIF, TIFF, bitmap, and the like.

Optical materials either intrinsically, or due to fogging or other environmental factors such as exposure to smoke, tend to impair visibility and thus reduce the so-called intensity of a given object or target viewed through the optical materials. In terms of apparatus 100, target 130 (FIG. 1), when viewed through a given optical material, will have an intensity $I_1$ (FIG. 4A), which is generally less than the actual intensity $I_0$ of target 130 when "viewed" directly by imaging system 110. Otherwise stated, the digital image 320A captured by imaging system 110 through a given optical material 120 includes an image of target 130 having an intensity $I_1$ that is generally less than the intensity $I_0$ that would have been captured by imaging system 110 if target 130 had been viewed directly by imaging system 110 rather than through the optical material 120.

Apparatus 100 can be used to test the reduction in intensity caused by the optical materials themselves without regard to additional environmental factors, such as respiration, fogging, exposure to smoke, etc. In such application, the reduction in intensity of target 130 depends on any number of factors associated with the optical material itself, such as its translucence, transparency, color, quality, and the like. Of course, in the event optical material 120 is impaired or obstructed by environmental conditions, such as condensation from humidity due to perspiration, respiration, and the like, apparatus 100 is also useful in assessing the corresponding reduction in intensity of target 130. In such applications, the target intensity is generally further reduced and can be thought of as assuming an intensity value $I_2$ of FIG. 4B, in which case a digital image 320B would have pixels associated therewith of intensity $I_2$.

Processing system 203 is operatively connected to imaging system 110 and is adapted to determine the intensities of one or more pixels in the digital image(s) of target 130. For example, processing system 203 can be suitably programmed to choose a target pixel corresponding to the center of target 130 and determine the gray scale intensity of such target pixel. Thus, when eight-bit grayscale is used, pixel intensity is characterized by a value from 0 to 255, with a higher number corresponding to a darker, that is, blacker pixel. One suitable tool or series of computer instructions for determining pixel intensity is the magic wand tool that is included as part of the IMAQ Vision Builder 6.0 software package (National Instruments), although any number of alternative computer programming steps or other tools may be used for determining target pixel intensity.

In order to determine the intensity of target 130 when viewed through optical material 120 under test, one or more target pixels may be analyzed by processing system 203 using the intensity determining software programming discussed previously. Thus, a mean intensity of target 130 may be determined by analyzing a plurality of target pixels in a region of interest, and similarly, a standard deviation of the intensity of a plurality of pixel pictures may likewise be determined.

Although any number of methods are suitable for selecting an appropriate set of target pixels, the magic wand tool or other suitable means can select a region of interest around a reference pixel in the digital image, such reference pixel being referred to as the origin. In this implementation, the origin is chosen as a pixel corresponding to the center of the target. The region of interest analyzed by processing system 203 is a polygon centered on the origin in which all the pixels have intensities within a given tolerance of the intensity of the origin. One suitable tolerance for defining the region of interest is twenty, that is, the region of interest will include pixels having an intensity value of plus or minus twenty in comparison to the intensity of the origin pixel. The coordinates of the region of interest are saved by the processing system and can be used for comparisons or other analysis as subsequent images from comparable regions are acquired and analyzed. Although any number of programming routines may be used to calculate mean intensity and standard deviation of pixels within the region of interest, one suitable tool for this task is the IVB Quantify Virtual Instrument, available from National Instruments.

As mentioned previously, apparatus 100 can be configurable in a variety of ways to test visibility through optical materials under a variety of environmental conditions, including variations in lighting, air temperature, air quality, fogging, humidity, and exposure to smoke. One testing configuration keeps constant the following components of apparatus 100 while digital images of target 130 are being captured: the headform 202, along with the positioning of its imaging systems 110, the position of the target 130, and the type of artificial lighting 212 (FIG. 1)). Holding such variables constant provides a baseline for determining intensities of target pixels of interest in the region.

Having discussed operation of apparatus 100 to determine intensity of target 130, methods and apparatus for testing, determining, or otherwise assessing visibility in relation to a readily understandable scale or index will now be discussed. As a preliminary matter, target intensity itself is generally not useful for quantifying visibility of optical materials. Preferably, different values of target intensity must be correlated with, calibrated to, or otherwise assigned a corresponding value or range of values indicating a visibility according to a relatively objective scale. One scale or indication of visibility is a so-called visual acuity index, such as the familiar Snellen index, including such values as 20/20, 20/40, 20/100, 20/200 and the like.

There are various ways and methods of associating intensity with a given visual acuity index, such as the Snellen index, to provide the requisite objective measure of visibility of the present invention. One method involves populating a table, database, or other data structure with calibrations or correlations of the intensity measured for target 130 seen through optical materials already associated with known values of visual acuity. This creates a suitable database or correlation file relating target intensity to visual acuity. Thus, for example, occlusion foils, such as Bangerter occlusion foils, are already associated with a visual acuity value or range expressed in terms of a known visual acuity index by the manufacturer of such foils. Such foils may be inserted into apparatus 100 and subjected to image capture therethrough in accordance with the procedures outlined above to determine the associated intensity of target 130. By using occlusion foils and other optical materials associated with different visual acuities in the range of the established visual acuity index, the correlation file or calibration table can be populated.

Another method for associating target intensity with visual acuity is to have one or more people with known visual acuities, such as 20/20 Snellen visual acuity, view an eye chart through the optical material, whether such optical material is "fogged" or otherwise obstructed, e.g., by exposure to smoke or soot. The human's visual acuity through the optical material is then measured by reference to the Snellen eye chart or other eye chart for evaluating visual acuity to assign a visual acuity value to such optical material. The same optical material is then used in testing apparatus 100 in such a way as to capture a corresponding digital image of target 130 and measure the corresponding intensity. In this way, the measured visual acuity is correlated or calibrated to a corresponding intensity. A series of such correlations with different optical materials is obtained and used to populate the file or database.

Figure 5:
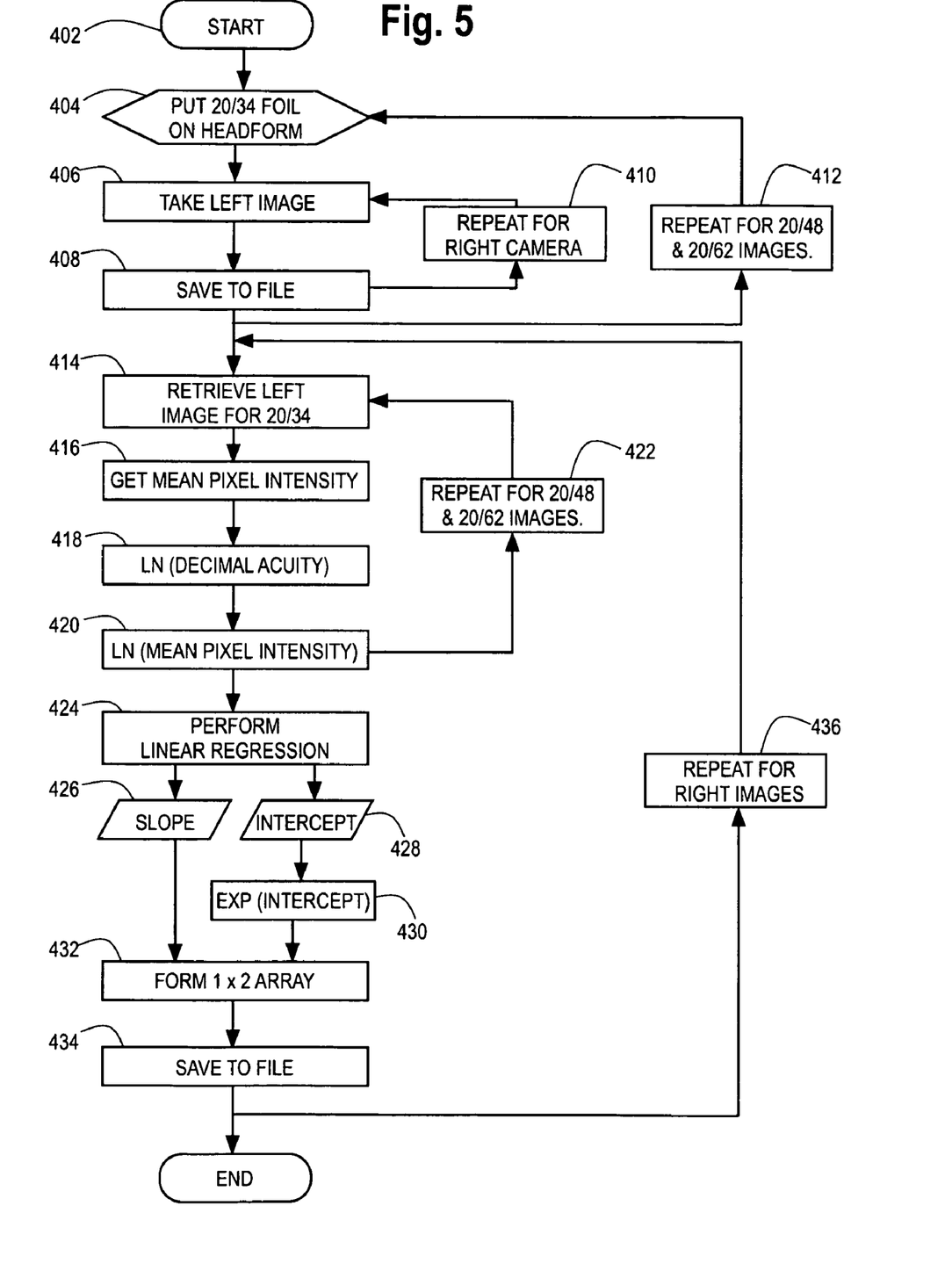
FIG. 5 is a flowchart of a method for calibrating target intensity to a known visibility index according to one aspect of the present invention.

One exemplary method of calibrating known or measured visual acuities to corresponding target intensities is diagramed in the flowchart of FIG. 5. The method begins at step 402. At step 404 a given optical material 120 (FIGS. 1 and 3) is placed between the imaging system 110 and the target 130. In this example of calibration, the optical material comprises Bangerter occlusion foils assigned a Snellen visual acuity index of 20/34, which is equal to a Snellen decimal visual acuity index of approximately 0.59. The Bangerter occlusion foils are mounted and positioned in operative relationship to apparatus 100 and imaging system 110 by any suitable means, such as headform 202 (FIGS. 1 and 2). At step 406 an image of the target as viewed through the optical material is digitally captured using an imaging system in the left eyehole of the headform. The digitally captured image is saved as a file, such as a JPEG file, or any other type of file (step 408). Optionally, the preceding steps (406 and 408) of capturing and saving images are repeated with an imaging system in the right eyehole of the headform (step 410). The process of capturing and saving images (steps 406 and 408) is repeated for different optical materials, and for the first and optional second imaging system as appropriate. Thus, after different occlusion foils are placed on headform 202 (step 404), images are taken and saved. The process occurs for occlusion foils assigned Snellen visual acuity value of 20/48 (Snellen decimal visual acuity of approximately 0.42), and then again with Bangerter occlusion foils assigned a Snellen visual acuity index of 20/62 (Snellen decimal visual acuity index of approximately 0.32) (steps 412).

After the desired number of images has been captured using the desired optical materials, the method proceeds to step 414 at which the digitally captured images, such as the image of the target captured by the imaging system in the left eyehole as viewed through the 20/34 occlusion foil, are retrieved. At step 416 the mean intensity of the pixels in a region of interest of the image are obtained, as described previously. At step 418, the natural logarithm of the decimal visual acuity value or index is calculated. At step 420 the natural logarithm of the mean pixel intensity, as determined in step 416, is calculated. At step 422, steps 414, 416, 418, and 420 are repeated for each of the digitally captured images for the various optical materials, as captured by an imaging system mounted in the left eyehole of the headform. At step 424, a linear regression is performed on the data set comprising the natural logarithm of the mean pixel intensities, as the independent variable, and the corresponding natural logarithm of the decimal visual acuity indices, as the dependent variable. Step 426 returns the slope of the regression. Step 428 returns the y-intercept of the regression. Step 430 applies the National Instruments Exponential Virtual Instrument to the intercept of the regression to return the exponential of the y-intercept returned in step 428. In step 432 a 1×2 array is formed comprising the slope from step 426 and the exponential of the y-intercept from step 430. At step 434 the 1×2 array is saved to a suitable file, such as a text file. The slope and the exponential of this relationship can be expressed as a correlation equation, or the correlation file or database previously discussed can be generated.

At step 436, steps 414-434 are repeated for the digitally captured images of the target as viewed through the various optical materials and captured by an imaging system mounted in the right eyehole of the headform. The analysis of these images provides further data correlating target intensity to Snellen visual acuity.

Once the calibration or correlation of target intensity to Snellen or other known visual acuity systems is determined, apparatus 100 is operable to determine a visibility value or visual acuity index for an optical material whose visibility has not been quantified. A digital image of target 130 viewed through optical material 120 is captured. The optical material 120 reduces the visibility by an unknown amount. An intensity value of the target is determined by any of the methods previously described herein and in connection with FIGS. 1-5. Using the determined target intensity, the visibility through the optical material is determined by accessing the correlating equation or correlation file which relates target intensity to a visual acuity index. More particularly, visibility is determined by using the measured target intensity to calculate the visual acuity index of the optical material from the equation relating slope and the exponential of the y-intercept (discussed above), or by using other mathematical operations, or look-up tables correlating target intensity to the visual acuity index. Suitable interpolation may be used to determine a visual acuity index or value corresponding to the measured target intensity when such measured intensity is not found in the correlation file or data structure. In another alternative, the measured target intensity is compared to one or more data points relating target intensity to visual acuity index of the correlation file, and a suitable range of associated visual acuity indices for the optical material under consideration is determined.

Figure 6:
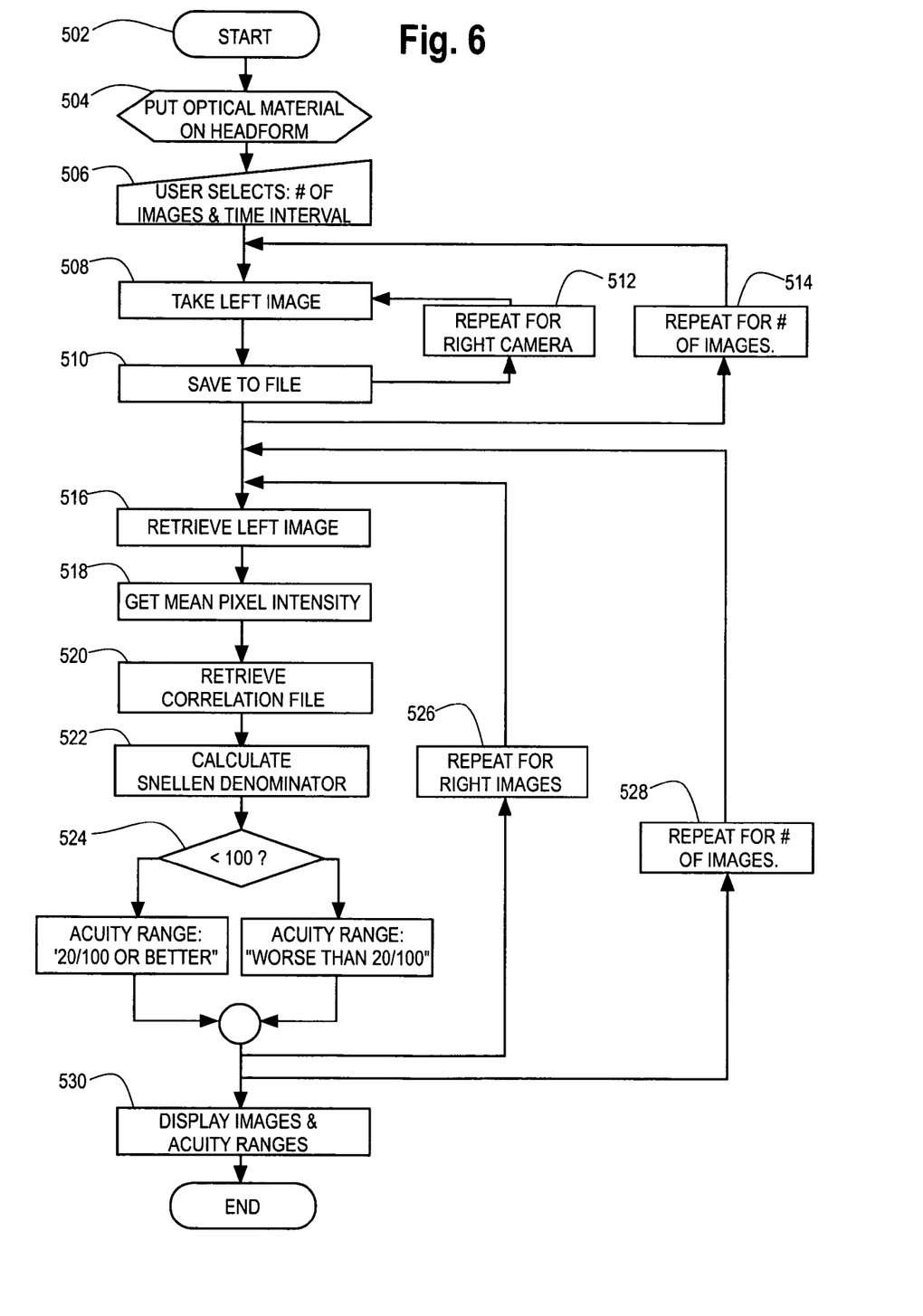
FIG. 6 is a flowchart of a method for assessing visibility through a given optical material according to one aspect of the present invention.

FIG. 6 is a flowchart of one suitable method for determining a quantifiable, visual acuity index or range of visibility for an optical material. The method starts at step 502. At step 504 any given optical material 120 is placed on headform 202. Optical material 120 is generally of a type to decrease the visibility of target 130 by an unknown amount, or is suitably obstructed by exposure to one or more environmental conditions such as smoke or fogging to decrease the visibility of target 130 by an unknown amount.

At step 506 the user selects the number of images of the target to be captured digitally by an imaging system. The user can also select the time interval between the images. At step 508 an image of the target is captured by an imaging system in the left eyehole of the headform. At step 510 the captured image is saved to a suitable file, such as a JPEG file. At step 512, steps 508 and 510 are repeated for an imaging system in the right eyehole of the headform. Steps 508, 510, and 512 are repeated at step 514 for the number of images chosen at step 506. At step 516 an image file is retrieved. For example, the image file corresponding to the image of the target captured by the imaging system in the left eyehole of the headform is retrieved.

At step 518 the mean intensity of pixels in a region of interest is determined for the retrieved image file by any suitable method, including those discussed herein. At step 520 the correlation file relating intensity to visual acuity is retrieved or otherwise accessed in a way to analyze the measured intensity. The measured mean pixel intensity is normalized in this implementation to parameters such as the distance from the imaging system to the target, the ambient lighting, and other parameters or variables, so that the comparison of the measured mean pixel intensity to the data in the correlation file or correlation equation will be meaningful.

At step 522 the denominator D of the Snellen visual acuity index (or value) associated with the optical material under analysis is calculated using the measured mean pixel intensity and data from the correlation file or correlation equation. More particularly, the denominator of the Snellen visual acuity index associated with the optical material is determined using the exponential of the intercept and the slope, as determined during the correlation phase discussed above, and the measured mean pixel intensity value. The equation for determining the denominator D thus, is formulated as $$D = \frac{20}{e^{(intercept)} \cdot (\text{mean pixel intensity value})^{slope}}$$

At step 524 the Snellen index determined using the foregoing evaluation is compared to a threshold Snellen index, such as 20/100, for this particular assessment. The acuity range index of the optical material is then returned. In one embodiment, a simple, pass or no-pass visibility standard evaluates whether the Snellen visual acuity index or range, returned from the above-described calculations, is either "20/100 or better" or "worse than 20/100". Step 526 repeats steps 516-524 for the images captured by the imaging system in the right eyehole of the headform. Step 528 then repeats steps 516-526 for the number of images selected at step 506. At step 530 the captured images and determined Snellen visual acuity index ranges are displayed by any suitable means, such as the graphical user interface of processing system 203.

The steps of FIG. 6 are preferably accomplished, at least in part, by computer instructions, software, firmware, microcode, or other programming for processing system 203. Such instructions may be written to a computer readable medium adapted to be loaded to the computer of processing system 203, which, in turn, is operable to perform the methods contained on the computer readable medium. The steps in FIGS. 5 and 6 are executable by any number of computer components of processing system 203, whether from the computer readable medium or, alternately, as instructions stored at suitable locations in memory of processing system 203. Computer 204 includes components and peripherals suitable for the variety of tests and assessments contemplated for apparatus 100, and likewise includes a display 209 and appropriate graphical user interface for displaying results and performing any of the various commands, inputs, operations, and the like.

In sum, visibility through an optical material can be determined from a target intensity measured through such material and a correlation equation that relates target intensity to a known visual acuity. Alternatively, the visibility can be determined by using the measured target intensity as an index into a table of visual acuities indexed by target intensities. The measured target intensity may be used to interpolate the table of visual acuity indexed by target intensity. In another embodiment, the measured target intensity can be compared to one or more source data points relating target intensity to visual acuity index to determine a range of the associated visual acuity index for the optical material.

The obstruction of optical material 120 can be on either side thereof or even within the optical material itself, and need not be in physical contact with the optical material. In the embodiment of FIGS. 1-5, the obstruction is formed by fog, i.e., by precipitation of moisture on the optical material. Thus, one use of the apparatus 100 is to measure the reduced visibility in goggles or masks due to fogging. However, other forms of environmental obstructions of optical material 120 can be analyzed with apparatus 100, including particulates that may be adsorbed or deposited onto the surface of optical material 120 such as sand, smoke, dust, dirt, and the like. In another embodiment, the obstruction may comprise integral obstructions, such as manufacturing defects in the optical material, including non-uniformities, tinting, impurities, or surface inequalities, such as scratches, pockmarks, and the like.

A number of embodiments of the invention have been described. Nevertheless, it will be understood that various modifications may be made without departing from the spirit and scope of the invention. For example, while certain examples of optical materials have been listed or described, it will be understood that the optical material can also be any other optical material associated with viewing or human vision. The optical material may be glass, plastic or any other material having suitable optical properties, and need not provide any degree of magnification. The optical material may be any shape, can have any surface contour, whether planar, or curved, or combinations; and can have any thickness, or even multiple thicknesses.

The imaging system has been described as a CCD camera, but can be any type of imaging system. Further, it will be understood that the target, although described as a circle, can by any shape. The target could alternately comprise multiple shapes to allow for assessment of optical parameters along multiple lines of sight between the imaging system and the target. In addition, various means of determining an intensity value of an image of a target have been described, but these are non-limiting. Any means of determining an intensity value may be used. While the target has been described as a gray-scale object, it can also be a colored object. The intensity of a colored object can be measured in a number of different ways. For example, the intensity can be measured as the intensity of a single color channel, such as the intensity of the red channel. Alternatively, the intensity can be measured as the average intensity or weighted average intensity of all of the color channels.

It should likewise be noted that, while apparatus 100 includes components to subject optical material 120 to humidity, fogging, respiration, or other environmental conditions, the methods and apparatus for assigning a quantifiable visibility to an optical material do not require such environmental components. In other words, a lens, glass, plate, visor, or other optical material, by its very nature, separate and apart from fogging, may act to decrease visibility, and the methods and apparatus described herein are suitable for assessing such decreases as well.

The many embodiments of the present invention provide one or more of the following advantages. The visibility through optical materials, including obstructed optical materials, can be objectively measured. This allows objective comparison of military equipment, safety equipment, fire equipment, and sports equipment under various environmental conditions. This also allows manufacturers to easily perform quality control tests of their optical products. Other advantages may be provided by the various embodiments discussed.

Accordingly, other embodiments are within the scope of the following claims.

What is claimed is:

1. An apparatus for assessing visibility through an optical material, the apparatus comprising:
    an imaging system including a target and a camera located and oriented for acquiring digital images of the target through the optical material, wherein the imaging system is adapted to capture multiple discrete digital images at different times;
    a system for exposing the optical material to one or more environmental conditions; and
    a processing system including programming for determining intensity of the target in the digital images, the programming further including operations relating the intensity of the target to a visual acuity index to assess the visibility through the optical material, wherein the processing system includes programming for determining the intensity of the target in the discrete digital images to assess changes in visibility through the optical material over time.

2. The apparatus of claim 1, further comprising a computer having a memory, and wherein the processing system includes programming to store the digital images in the memory.

3. The apparatus of claim 1, further comprising programming for relating optical materials having known visual acuities to respective intensities of the target to develop at least one of a correlation file or a correlation equation.

4. The apparatus of claim 3, wherein the processing system includes programming for determining a Snellen visual acuity index for the optical material by using the intensity and at least one of the correlation file or the correlation equation.

5. The apparatus of claim 1, wherein the programming for determining intensity of the target includes operations for determining intensity of at least one pixel located in the area of the target.

6. The apparatus of claim 1, wherein the system for exposing the optical material to one or more environmental conditions comprises a system for fogging the optical material to cause condensation to accumulate thereon.

7. The apparatus of claim 1, further comprising a headform operatively associated with the imaging system and the system for exposing the optical material to one or more environmental conditions.

8. The apparatus of claim 1, wherein the system for exposing the optical material to one or more environmental conditions comprises a system for exposing the optical material to smoke.

9. A method of assessing visibility through an optical material, comprising:
   acquiring a digital image of a target through the optical material;
   determining an intensity of the target; and
   using the determined target intensity to determine a visual acuity index of the optical material, wherein determining the visual acuity index of the optical material comprises using the determined target intensity to interpolate a table of visual acuity indexed by target intensity, the visual acuity index corresponding to the visibility through the optical material.

10. The method of claim 9, wherein determining the intensity of the target comprises determining an intensity value of at least one target pixel in the digital image.

11. The method of claim 9, wherein determining the intensity of the target comprises determining a mean intensity value of a plurality of target pixels in the digital image.

12. The method of claim 9, wherein determining the visual acuity index of the optical material comprises calculating the visual acuity index using an equation relating visual acuity to determined target intensity.

13. The method of claim 9, further comprising obstructing the optical material by exposing it to one or more environmental conditions prior to capturing the digital image.

14. The method of claim 13, wherein the step of obstructing the optical material comprises fogging the optical material.

15. The method of claim 13, wherein the step of obstructing the optical material comprises exposing the optical material to smoke.

16. A method for correlating acuity to a visual property of a target, the method comprising:
   capturing a first digital image of the target through a first optical material having a corresponding first visual acuity index;
   capturing a second digital image of the target through at least one of the following: the first optical material obstructed to have another visual acuity index different from the first visual acuity index, or a second optical material with a corresponding, second visual acuity index different from the first visual acuity index;
   determining respective target intensities for the captured digital images;
   relating the target intensities of the captured digital images to the visual acuity indices of the optical materials through which the digital images were captured, thereby correlating visibility through the optical materials with the target intensity of the captured digital images.

17. The method of claim 16, wherein the step of capturing the digital images comprises capturing digital images of a circular target.

18. The method of claim 16, wherein the steps of capturing the digital images include capturing the images through an optical material having a Snellen visual acuity index associated therewith.

19. The method of claim 16, wherein the steps of capturing the digital images includes capturing the digital image through an optical material comprising a non-magnifying lens for a protective mask.

20. The method of claim 16, wherein the step of determining respective target intensities includes determining an intensity value of a target pixel in the digital image.

21. The method of claim 16, wherein the steps of determining respective target intensities comprises determining a mean intensity value of a plurality of target pixels in the digital image.

22. The method of claim 16, wherein the step of relating the target intensities to the visual acuity indices includes developing a correlation equation from the visual acuity indices and the target intensities by performing a linear regression.

23. The method of claim 16, wherein the step of relating the target intensities to the visual acuity indices includes developing a correlation look-up table from the visual acuity indices and the determined target intensities.

* * * * *